(12) United States Patent
Cho et al.

(10) Patent No.: US 6,600,094 B1
(45) Date of Patent: Jul. 29, 2003

(54) **RECOMBINANT PLANT EXPRESSION VECTOR COMPRISING ISOLATED CDNA NUCLEOTIDE SEQUENCE ENCODING FARNESYL PYROPHOSPHATE SYNTHASE (FPS) DERIVED FROM SEEDLINGS OF SUNFLOWER (*HELIANTHUS ANNUS*)**

(75) Inventors: Jeong-Woo Cho, Kwangju (KR); Sun-Chung Park, Kwangju (KR); Hyun-Sook Kil, Iksan (KR); Chang-Ho Chung, Kwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/353,227

(22) Filed: Jul. 14, 1999

(30) Foreign Application Priority Data

Jun. 22, 1999 (EP) .............................. 99202021

(51) Int. Cl.$^7$ ......................... A01H 5/00; C12N 1/16; C12N 1/21; C12N 15/74; C12N 15/81; C12N 15/82
(52) U.S. Cl. ............................... 800/317.3; 435/252.2; 435/252.3; 435/254.2; 435/320.1; 435/468; 435/471; 800/278; 800/290; 800/298
(58) Field of Search .................. 435/69.1, 320.1, 435/468, 419; 536/23.2, 23.6; 800/278, 290, 298

(56) References Cited

U.S. PATENT DOCUMENTS 5,929,304 A * 7/1999 Radin et al. ................ 435/183
6,242,227 B1 * 6/2001 Millis et al. ................ 435/125

OTHER PUBLICATIONS

Hill et al., Functional Analysis of Conserved Histidines in ADP–Glucose Pyrophosphorylase from *Escherichia coli*, 1998, Biochemical and Biophysical Commun., vol. 244, pp. 573–577.*
Guinto et al., Unexpected crucial role of residue 225 in serine proteases, Mar. 1999, Proc. Natl. Acad. Sci., vol. 96, pp. 1852–1857.*
Alberghina, Protein Engineering in Industrail Biotechnology, pp. 8–9.*
Rothstein, et al., "Promoter cassettes, antibiotic–resistance genes, and vectors for plant transformation", Gene, vol. 53, pp. 153–161, 1987.*
Gen Bank Accession No. AF019892, Aug. 18. 1997.*
He, Zhili et al. (1997); "Ribulose–1,5–Bisphosphate Carboxylase/Oxygenase Activase Deficiency Delays Senescence of Ribulose–1,5–Bisphosphate Carboxylase/Oxygenase but Progressively Impairs Its Cataysis during Tobacco Leaf Development"; Plant Physiol.; vol. 115; pp. 1569–1580.
Oh, Sung Aeong et al. (Apr. 17, 1997); "Identification of three genetic loci controlling lead sebescence in *Arabidopsis thaliana*"; The Plant Journal; vol. 12, pp. 527–535.

Cunillera, Nuria et al. (Jan. 3, 1996); "*Arabidopsis thaliana* Contains Two Differentially Expressed Farnesyl–Diphosphate Synthase Genes"; The Journal of Biological Chemistry; vol. 271; No. 13;pp. 7774–7780.
Ding, Biao et al. (Feb. 17, 1993); "Correlation between arrested secondary plasmodesmal development and onset of accelerated leaf senescence in yeast acid invertase transgenic tobacco plants"; The Plant Journal; vol. 4, pp. 179–189.
Chambon, C. et al. (Apr. 13, 1990); "Isolation and properties of yeast mutants affected in farnesyl diphosphate synthetase"; Current Genetics; vol. 18; pp. 41–46.
Wilkin, Douglas J. et al. (Aug. 23, 1989); "Isolation and Sequence of the Human Farnesyl Pyrophosphate Synthetase cDNA"; The Journal of Biological Chemistry; vol. 265; No. 8; pp. 4607–4614.
Thom, Julia R. et al. (Sep. 19, 1988); "Role of the Leader Peptide of Maltose–Binding Protein in Two Steps of the Export Process"; Journal of Bacteriology; vol. 170; No. 12; pp. 5654–5661.
Light, David R. et al. (Jun. 2, 1989); "Rubber Elongation by Farnesyl Pyrophosphate Synthases Involves a Novel Switch in Enzyme Stereospecificity"; The Journal of Biological Chemistry; vol. 264; No. 31; pp. 18586–18607.
Vitale, Mario et al. (Jun. 24, 1998); "Prenyltransferase Inhibitors Induce Apoptosis in Proliferating Thyroid Cells through a p53–Independent, CrmA–Sensitive, and Caspase–3–Like Protease–Dependent Mechanisms"; Endocrinology; vol. 140; No. 2; pp. 698–704.
Kohl, Nancy E. et al. (Jun. 25, 1993); "Selective Inhibition of ras–Dependent Transformation by a Farnesyltransferase Inhibitor"; Science; vol. 260; pp. 1934–1936.

* cited by examiner

Primary Examiner—Amy J. Nelson
Assistant Examiner—Russell Kallis
(74) Attorney, Agent, or Firm—Mathews, Collins, Shepherd & McKay, P.A.

(57) ABSTRACT

The present invention provides nucleotide and peptide sequences of an isolated cDNA coding for sunflower farnesyl pyrophosphate synthase, a key enzyme for the structurally diverse class of isoprenoid biosynthetic metabolites. The present invention also provides the recombinant plant expression vector comprising said nucleotide sequences and for the host cell into which said DNA sequence in the recombinant plant expression vector has been introduced to produce transgenic tobacco plants. Transgenic plants expressing heterologous farnesyl pyrophosphate synthase show 2-fold increase in seed production, higher chlorophyll contents in leaves as compared to non-transgenic or control vector-transformed tobacco plants. The expression vector for the sunflower farnesyl pyrophosphate synthase gene, herein designated pCIP-sfps, has been deposited with the Korea Research Institute of Bioscience and Biotechnology Korean Collection for Type Cultures (K.C.T.C.) designation number KCTC 0520BP, having been deposited on Sep. 7, 1998.

14 Claims, 8 Drawing Sheets

(4 of 8 Drawing Sheet(s) Filed in Color)

SEQUENCE LISTING

```
<160> NUMBER OF SEQ ID NOS: 5

<210> SEQ ID NO 1
<211> LENGTH: 2075
<212> TYPE: DNA
<213> ORGANISM: Helianthus annus
<300> PUBLICATION INFORMATION:
<308> DATABASE ACCESSION NUMBER: AF019892
<309> DATABASE ENTRY DATE: 1997-08-16
```

-continued

<313> RELEVANT RESIDUES: (1)..(1347)

<400> SEQUENCE: 1

| | | | | | |
|---|---|---|---|---|---|
| cattttctcg | gttcaaaatc | gttattcctg | taatatattg | atccatccca | cgatcttctt | 60 |
| ttcttggtcg | tcttctgaaa | cgctaatcgg | atccagaagc | catggacaaa | agcatcagca | 120 |
| tcacctccaa | cgttagcacg | acgacttcca | tggaaaagat | cgaccacgcc | gctagctgga | 180 |
| tcagcgcaac | cgtaatatcc | gctttcttca | cctccctcga | acgctgcgcc | tgcgtcaatc | 240 |
| tctccacctc | tcatgacgac | gacgacgacg | acgacgacga | atcccatcac | cgtcctctcg | 300 |
| ctctctccgc | cgctcctcat | ccaaacgaca | ccgtttagct | ctgttttta | acctctggta | 360 |
| atttataaat | ttaatccctc | gtttgtttct | tttgataatc | gattggtgtg | gatttgtaat | 420 |
| ttcttgattt | gaaatgtat | gtctactgtg | tgtaaatgtg | catgtctcag | aatttgattg | 480 |
| ttttgcgtgt | atctgacttt | atatacttgg | gtttaaaatc | agaatgaatc | atcgttttg | 540 |
| catttacatt | gaaaaaatat | caagaagaga | atttggtaga | gatcatttgt | ttgttttgaa | 600 |
| gttttctttt | gtgatcaatg | tttctcgatt | tacctttttc | atttcatttc | tgatctctgc | 660 |
| gttcaactat | taaaaccgga | acagcatcag | tttcatgttt | tattttgtca | atgtgtcaga | 720 |
| gatcctgtca | ctttagattt | catagtttca | aaagtgatta | tttgatcatg | tgggtccctg | 780 |
| ctgtgagaac | cagtgggcac | tggccttag | tttggttaaa | agcaggattc | aaaacttcat | 840 |
| actagtttct | ttgttctaaa | atgtatttag | cctttttcaa | actcaagttg | cacttgttgt | 900 |
| acaaaagaca | cttttctttt | gaatctaatt | taacattaca | ttcaaaaaaa | aaaaaaactt | 960 |
| catactaagt | aaatgtcgtg | tttgatccaa | acttttccca | atttgtttgc | ttagcagggt | 1020 |
| gcaatcttgt | ttaaatatct | ttgtcatgta | taatgtgatt | ccatctcttc | atccatatag | 1080 |
| agaaaatctt | gtttaaatgt | cttttgtcat | atgaccatat | tctcacttgg | gtttctagaa | 1140 |
| aaagttttgg | gttcttgag | tttgttgaat | tggatctcct | tatggcttag | accgtcgttc | 1200 |
| caactgctga | agaagcaagt | atgttgactc | aaaacagtca | cgttatatct | ctgtctcttt | 1260 |
| gataattctt | ggcttttatg | tgttgggtgc | ctagtatcat | ttgtttaaa | ggtttaggga | 1320 |
| acaaaggtc | ataaactata | ataagaatac | ttttacaat | gttatttcct | cagcaaaagt | 1380 |
| agcacgcatt | cacattctcc | aagtttcatc | atttgttatt | tatgaacgca | aacaaaaaaa | 1440 |
| ctgtactatt | aacaagcttt | tgttaagaaa | aaagtaagga | accctctta | ggatatgtat | 1500 |
| gtttcaacaa | taagcttata | tctttactca | ttaagcccac | tagacaactt | tgtgagatag | 1560 |
| atcttataag | aagcgtatca | ctttatcccc | gtgattactt | ctcaaaacaa | cgagttttga | 1620 |
| tttgtgctac | tttattaaat | tcacgttctg | ttttcagaaa | ttttgttttt | tctgataggt | 1680 |
| tcgtattgaa | attgacctct | ttggaaactg | gatctttcat | aagatagaaa | gagaggtccc | 1740 |
| catttcccaa | gttatcaaa | caaaagaaa | aaaaatcta | aattgttctc | atcttgagac | 1800 |
| aaccaatcag | aatgaaccat | ctgagtcagc | caaagggttt | aatagtcacc | atttgccaat | 1860 |
| tgtattcata | ctcttcctt | tttggtgcgt | tattctaaga | gccctagtca | gaattcaaac | 1920 |
| atttggcaat | gaaatcatac | aaacttaata | accctaattt | actcatctcc | acgcacacac | 1980 |
| ataataaact | cttcttatcc | tcttctccat | tcaatctctt | attctctttt | ccttccttca | 2040 |
| tataccttaa | acagcaacgt | tctctgttct | tcttc | | | 2075 |

<210> SEQ ID NO 2
<211> LENGTH: 341
<212> TYPE: PRT
<213> ORGANISM: Helianthus annus

<400> SEQUENCE: 2

```
Met Ala Ser Asp Leu Lys Ser Lys Phe Leu His Val Tyr Gln Thr Leu
  1               5                  10                  15
Lys Ser Glu Leu Leu Asn Asp Pro Ala Phe Glu Phe His His Asp Ser
             20                  25                  30
Arg Gln Trp Ile Asp Lys Met Leu Asp Tyr Asn Val Pro Gly Gly Lys
         35                  40                  45
Leu Asn Arg Gly Leu Ser Val Val Asp Ser Tyr Gln Leu Leu Lys Gly
     50                  55                  60
Ala Glu Leu Thr Asp Asp Glu Ile Phe Leu Ala Ser Ala Leu Gly Trp
 65                  70                  75                  80
Cys Ile Glu Trp Leu Gln Ala Tyr Phe Leu Val Leu Asp Asp Ile Met
                 85                  90                  95
Asp Gly Ser His Thr Arg Arg Gly Gln Pro Cys Trp Phe Arg Leu Pro
            100                 105                 110
Lys Val Gly Met Ile Ala Ala Asn Asp Gly Leu Ile Leu Arg Asn His
            115                 120                 125
Val Pro Arg Ile Leu Lys Lys His Phe Arg Gly Lys Pro Tyr Tyr Val
    130                 135                 140
Asp Leu Val Asp Leu Phe Asn Glu Val Glu Phe Gln Thr Ala Ser Gly
145                 150                 155                 160
Gln Met Ile Asp Leu Ile Thr Thr Leu Val Gly Glu Lys Asp Leu Ser
                165                 170                 175
Lys Tyr Ser Leu Ser Ile His Arg Arg Ile Val Gln Tyr Lys Thr Ala
            180                 185                 190
Tyr Tyr Ser Phe Tyr Leu Pro Val Ala Cys Ala Leu Leu Met Phe Gly
        195                 200                 205
Glu Asp Leu Asp Asn His Val Glu Val Lys Asn Val Leu Val Glu Met
    210                 215                 220
Gly Thr Tyr Phe Gln Val Gln Asp Asp Tyr Leu Asp Cys Phe Gly Ala
225                 230                 235                 240
Pro Glu Val Ile Gly Lys Ile Gly Thr Asp Ile Glu Asp Phe Ser Ser
                245                 250                 255
Trp Leu Val Val Lys Ala Leu Glu Leu Ala Asn Glu Glu Gln Lys Lys
            260                 265                 270
Val Leu His Glu Asn Tyr Gly Lys Lys Asp Pro Ser Ser Val Ala Lys
        275                 280                 285
Val Lys Glu Leu Tyr Asn Thr Leu Asn Leu Gln Gly Val Phe Glu Asp
    290                 295                 300
Tyr Glu Ser Thr Ser Tyr Lys Lys Leu Ile Thr Ser Ile Glu Gly His
305                 310                 315                 320
Pro Ser Lys Ala Val Gln Ala Val Leu Lys Ser Phe Leu Gly Lys Ile
                325                 330                 335
Tyr Lys Arg Gln Lys
            340
```

<210> SEQ ID NO 3
<211> LENGTH: 33
<212> TYPE: DNA
<213> ORGANISM: Artificial Sequence
<220> FEATURE:
<223> OTHER INFORMATION: Degenerate primers for DNA amplification

<400> SEQUENCE: 3

```
                                                                -continued cargchtwyt tycttgtdct tgatgayath atg                                    33

<210> SEQ ID NO 4
<211> LENGTH: 29
<212> TYPE: DNA
<213> ORGANISM: Artificial Sequence
<220> FEATURE:
<223> OTHER INFORMATION: Degenerate primers for DNA amplification

<400> SEQUENCE: 4
tkmacsacya wccaagarca tytraaatc                                         29

<210> SEQ ID NO 5
<211> LENGTH: 24
<212> TYPE: DNA
<213> ORGANISM: Artificial Sequence
<220> FEATURE:
<223> OTHER INFORMATION: Degenerate primers for DNA amplification

<400> SEQUENCE: 5
tcgcgaggcg aattgggtac cggg                                              24
```

RECOMBINANT PLANT EXPRESSION VECTOR COMPRISING ISOLATED CDNA NUCLEOTIDE SEQUENCE ENCODING FARNESYL PYROPHOSPHATE SYNTHASE (FPS) DERIVED FROM SEEDLINGS OF SUNFLOWER (HELIANTHUS ANNUS)

BACKGROUND OF THE INVENTION

1. Field of Invention

The present invention is directed to provide a recombinant plant expression vector containing isolated cDNA nucleotides sequence encoding sunflower farnesyl pyrophosphate synthase (SFPS) derived from seedlings of *Helianthus annus*, and also to produce transgenic tobacco plants conferring delayed senescence, greater flower development and increased seed production.

2. Description of the Prior Art

The enzyme farnesyl-pyrophosphate synthase (FPS) catalyzes the synthesis of farnesyl pyrophosphate from isopentenyl pyrophosphate and dimethylallyl pyrophosphate. Farnesyl pyrophosphate (FPP) synthase is a key enzyme in isoprenoid biosynthesis that supplies C15 precursors for the structurally diverse classes of essential metabolites, such as sterols, carotenoids, and prenyl quinones, especially in steroidogenesis and carotenogenesis. The isoprenoid biosynthetic pathway is built around a family of pyrophosphate esters of linear alcohols that contain an increasing number of isoprene units. Beginning with the C5 molecule (DMAPP and IPP), a series of C10 (GPP), C15 (Farnesyl pyrophosphate), C20 (GGPP) and higher molecular weight isoprenoid pyrophosphates are formed by the 1'-4' addition of isopentenyl pyrophosphate to the growing chain. The 1'-4' condensation reactions are catalyzed by a family of prenyltransferases that are highly selective for the chain length and a double bond stereochemistry of both substrates and products. FPP is the precursor of the structurally diverse class of sesquiterpenoids such as phytoalexins and lies at a multiple branch point of the isoprenoid pathway, especially in steroidogenesis and carotenogenesis. Several thousands of natural plant products are known to originate from the isoprenoid pathway including chlorophylls, vitamins A, E and K, gibberellines, abscisic acid. Also, previous studies showed that the involvement of FPS in the final steps of natural rubber biosynthesis which includes polymerization of isopentenyl pyrophosphate into rubber. FPS genes have been reported previously in different organisms, including human (Wilkin et al., J. Biol. Chem. 1990 265(8): 4607–4614), yeast (Chambon et al., Curr. Genet. 1990 18(1): 41–46), *Arabidopsis thaliana* (Cunillera et al., 1996 J. Biol. Chem. 271, 7774–7780), rubber tree (Light et al., J. Biol. Chem. 1989 264(31): 18598–607), and *E. coli* (Fujisaki et al., J. Bacteriol. 1989 171(10): 5654–5658). Isoprenylation is a posttranslational modification that is believed to be necessary, but not sufficient, for the efficient association of numerous eukaryotic cell proteins to membranes. Additional modifications have been shown to be required for proper intracellular targeting and for the function of certain isoprenylated proteins in mammalian and yeast cells. Attachment of the prenyl groups farnesyl and geranylgeranyl to specific eukaryotic cell proteins by protein prenyltransferases is required for the functioning of a number of cellular processes including signal transduction.

Protein farnesyltransferase (FTase) catalyzes the transfer of the hydrophobic farnesyl group from farnesyl pyrophosphate (FPP) to cellular proteins such as Ras at a cysteine residue near their carboxy-termini. This process is necessary for the subcellular localization of these proteins in the plasma membrane and is required for the transforming activity of oncogenic variants of Ras, making the FTase a prime target for anticancer therapeutics. Farnesylation is required for the membrane partition and function of several proteins, including Ras. Farnesyl-protein transferase inhibitors (FTIs) were developed to prevent Ras processing and for the treatment of cancers harboring mutated Ras. Thus, the inhibitors of protein prenylation have been proposed for the chemotherapy of tumors (Vitale et al., Endocrinology 1999 140(2): 698–704; Kohl et al., Science 1993 260(5116): 1934–1937). Transgenic plants expressing heterologous farnesyl pyrophosphate synthase show two fold increase in seed production, higher chlorophyll contents in leaves and stronger drought-stress tolerance, as compared to non-transgenic or control vector-transformed tobacco plants.

Comparison of the amino acid sequences of FPS ranging from plants to human has shown five distinct regions with high similarity. As a first step to characterize the function of FPS, we have cloned a FPS cDNA and shown that it encodes a functional FPS. The 35S promoter fused to the sunflower SFPS (KCTC 0520BP), which encodes the enzyme farnesyl pyrophosphate synthase, was introduced and the morphological changes were examined in the transgenic tobacco plants (*Nicotiana tabacum* L.). These constructs allowed the overproduction of farnesyl pyrophosphate (fpp) in tobacco in a random manner. Overproduction of fpp produced a few notable morphological and physiological changes in $T_0$ plant, including darker pigmentation in leaves, new shoot initiation, sustained growth, prolonged and delayed senescence in leaves followed by normal seed settings, more than doubling of flowers, and at least 2-fold increase in seeds production. We tested whether an increased production of the fpp in any organs can influence developmental events, such as growth of axillary shoot meristems, flowering, and seed setting or leaf senescence, in the plant.

Enhanced plant growth and yield has been a major goal of the crop science field. It has been hard to achieve since growth and development is governed by a complex interplay of different genes and their products. One way to increase the productive capacity of biosynthesis would be to apply recombinant DNA technology.

The skills described in this invention will give the agricultural advantages inherent in the transgenic plants as described below. The method this invention includes introducing the sense strand construct of pFPS, regenerating the plant transcribes the nucleotide sequence, and selecting plants which showing dramatic changes in the plant life span, overall seed yield, flower numbers and chlorophyll content. The recombinant expression cassette can be introduced into the plant tissue using Agrobacterium or by a sexual cross.

This invention further provides methods of conferring enhanced growth and development. Although this invention described in conjunction with tobacco plants, these skills may also be used to control growth and development in plants other than tocacco plants.

SUMMARY OF THE INVENTION

An object of the present invention concerning the Farnesyl Pyrophosphate Synthase (FPS) of sunflower (*Helianthus annus*) herein is:

(a) to amplify and sequence sunflower FPS cDNAs by using a pair of universal FPS oligonucleotides probe, (b) to express FPS cDNAs in bacterial cells and to carry out functional complementation assay in yeast mutant to verify its function, (c) to generate a line of transgenic tobacco plants to observe the influences of the overexpression of sunflower Farnesyl Pyrophosphate Synthase (SFPS) in vivo, (d) to produce more numbers of flowers in the plant life time and to produce more than double amounts of seeds in the transgenic plants, The present invention provides nucleotide and peptide sequences of an isolated cDNA coding for sunflower farnesyl pyrophosphate synthase, a key enzyme for the structurally diverse class of isoprenoid biosynthetic metabolites. The present invention also provides the recombinant plant expression vector comprising said nucleotide sequences and for the host cell into which said DNA sequence in the recombinant plant expression vector has been introduced to produce transgenic tobacco plants.

BRIEF DESCRIPTION OF THE DRAWINGS

The patent file contains at least one drawing executed in color. Copies of this patent or patent application publication with color drawing(s) will be provided by the Office upon request and payment of the necessary fee.

Other objects and aspects of the invention will become apparent from the following description of embodiments with reference to the accompanying drawings in which.

EXAMPLE 1 cDNA Cloning

Figure 1:
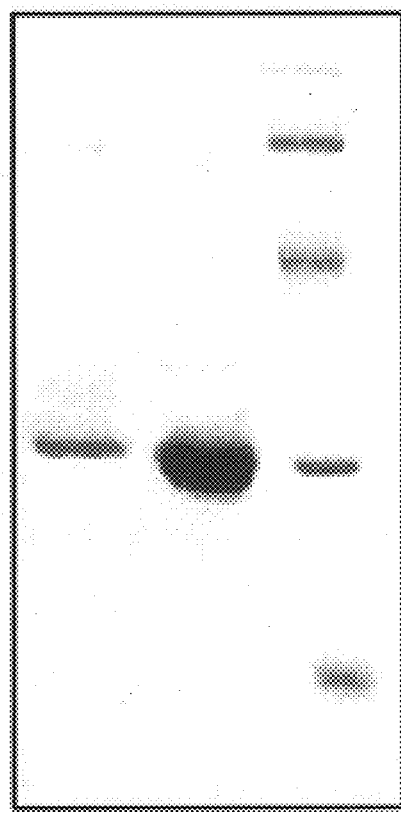
FIG. 1 depicts the patterns of the expressed sun flower farnesyl pyrophosphate synthase protein in *Escherichia coli* on a Coomasie Blue stained gel. In each lane, 10 μg of protein was loaded and separated on a 10–20% Gradient SDS-polyacrylamide gel electrophoresis, followed by Coomasie Blue staining for visualization. Lane 1, clone 1; lane 2, clone 2; and lane 3; molecular weight marker. Arrow indicates a band of overexpressed protein (Mr 31,000).

The gene for the farnesyl pyrophosphate synthase herein was isolated as follows: all the chemicals used in this works were purchased from Sigma if not mentioned. Leaves from 10 days old seedlings were used for constructing sunflower λgt10 cDNA library using Stratagene cDNA synthesis kit. This library was originally plated and subsequently amplified on *E. coli* XL1-Blue MRF' strain. SOL-R (Stratagene) competent cells kept in 30% Glycerol at −90° C. were plated on LB/tetracycline plates for selection and incubated overnight at 37° C. incubator. Well-isolated single colony was inoculated in 50 ml sterilized LB supplemented 0.2% maltose and 2 mM $MgSO_4$. The culture was grown overnight at 37° C. with shaking (250 rpm in a rotary shaker). Bacteria grown in the maltose adsorb λ phage more efficiently; the maltose induces the maltose operon, which contains the gene (lamB) that codes for the bacteriophage λ receptor. Because of their instability SOL-R cells were kept in LB medium at 4° C. until needed. Transfer 5 ml of SOL-R cells into Eppendorf tubes and spin for 8 sec at the full speed in a microfuge. Cells were resuspended in 2.5 ml of 10 mM $MgSO_4$ and their density was read at $OD_{600}$. $10^5$ pfu of bacteriophage of cDNA library were added to the Falcon tubes (13 mm×100 mm) containing 0.1 ml of diluted bacterial cells ($10^8$ cells/ml) and vortexed briefly. The tubes were incubated at 37° C. for 20 min to allow the phage particles to adsorb to the bacteria. While phages and bacterial host cells were incubating, 0.7% Top agarose in LB was melted and adjusted to 47° C. in a water bath (Precision). After incubation 8 ml of molten Top agarose was added to each tube, vortexed lightly, and overlaid on top of NZY bottom agar plates. The plates were swirled carefully for even distribution of bacteria and left for 10 min to allow the top agarose to harden. Then, the plates were moved to 37° C. incubator, inverted and allowed to grow 7~8 hours. After 7 hours plaques were checked and incubating was continued a few more hours to obtain confluently lysed plates. To confluent plates, 8 ml of SM (10 mM NaCl/10 mM $MgSO_4 7H_2O$/50 mM Tris, pH 7.5/0.01% Gelatin) was added and the plates were shaken for 1 hour at 4° C. The fluids were transferred to tubes and spun at 2,000 rpm for 3 min at 4° C. to precipitate debris. The supernatants were transferred to new tubes and 50 μl of DNase and RNase (10 mg/ml respectively) were added. The samples were left overnight at 4° C. Equal volume of 2 M NaCl and 20% PEG (mw 8,000) in SM was added, vortexed, and incubated on ice for 3 hours. Then, tubes were spun at 12,000 rpm for 20 min at 4° C. After removing the supernatants, the pellets were resuspended in 500 μl of SM without NaCl and Gelatin and 25 μl of 20% SDS and 40 μl of 0.5 M EDTA, pH 7.5 were added. The suspensions were briefly vortexed and incubated at 65° C. for 10 min to lyse virus. The lysates were then cooled down to room temperature and 500 μl of PCI (Tris-saturated phenol: chloroform: Isoamylalcohol= 25:24:1) were added to each tube and spun at 5,000 rpm for 5 min. The supernatants were carefully transferred to new tubes and equal volumes of chloroform were added. After spinning at 5,000 rpm for 5 min, supernatants were saved and mixed with 3 volumes of EtOH with 2 M ammonium acetate. Overnight incubation at −20° C. produced approximately 1 mg of restriction enzyme digestible DNA in each tube.

Electrophoresis was routinely carried out to separate, identify, and purify nucleic acid on the basis of size using various concentrations of agarose gels (0.7~1.5%). Horizontal mini gel apparatus (BRL) was mainly used. The open ends of the plastic tray in the gel box were sealed with two pieces of tape and set on the bench. The correct amount of the agarose and 1×TAE (40 mM Tris-acetate/1 mM EDTA, pH 8.0) were added to a Erlenmeyer flask and placed on a Mettler scale to be weighed. Then the slurry was boiled in a microwave oven until the granules of the agarose completely dissolved, with gentle swirling occasionally. The agarose gel solution was weighed again and adjusted to its original volume by adding $H_2O$ on a Mettler. Proper amount of EtBr (0.5 µg/ml) was added and the gel was poured into the plastic tray with a desired comb. After the gel was set, the comb and tapes were removed. Then, the tank was filled with 1×TAE just enough to cover the gel to a depth of about 1 mm. The DNA samples were mixed with gel loading buffer (0.25% Bromophenol blue/0.25% Xylene cyanol FF/15% Ficoll) heated for 5 minutes at 65° C. and cooled on ice and loaded using a automatic pipette. The gel was run at a voltage of 5 V/cm until the Bromophenol blue reached to 1 cm away from cathode end of the gel. The gel was then examined on an UV light illuminator (Fotodyne) and photographed using a Polaroid (ASA 3,000) high sensitive film.

EXAMPLE 2

Polymerase Chain Reaction Using Degenerate Primers

We developed a universal oligonucleotide probe based on the reported FPS sequences which was used for PCR amplification using a λZAP cDNA library made with adult leaf mRNA. The sequences of the degenerate primers used for enzymatic amplification of farnesyl pyrophosphate synthase were following:

Primer 1 (SEQ ID NO:3): 5'- CAR GCH TWY TTY CTT GTD CTT GAT GAY ATH ATG -3'

Primer 2 (SEQ ID NO:4): 5'- TKM ACS ACY AWC CAA GAR CAT YTR AAA TC -3'.

Total plasmid DNA extracted from a pool of cDNA library, 1 µg, was used in a 50 µl reaction mixture containing 5 µM of primers 1 and 2, 0.2 mM dNTPs, 1.5 mM MgCl$_2$, 10 mM Tris, pH 8.3, 50 mM KCl, and 2.5 u Taq polymerase. The samples were overlaid with a drop of sterilized mineral oil to minimize evaporation. The first cycle was run at the condition of 2 min 94° C., 1.5 min 50° C., 3 min ramp to 72° C., 1.5 min 72° C. The next two cycles were run 1 min at 94° C., 1.5 min 50° C., 3 min ramp to 72° C., and 1.5 min 72° C. After these preruns, 32 cycles of amplifications were carried out at 1 min 94° C., 1.5 min 55° C., 1.5 min ramp to 72° C., and 1.5 min 72° C. From the PCR products, 10 µl of aliquots were mixed with same amount of loading buffer and separated on a 1% Agarose gel.

EXAMPLE 3

Nucleotide Sequencing of the Amplified Nucleic Acid Fragments

Subcloning of PCR Products

Cloning of PCR products as blunt ended fragments has been very inefficient, due to the template independent terminal transferase activity of Taq polymerase, which results in the addition of a nucleotide at the 3' end of the fragment. In most cases, it is adenosine because of the strong preference of the polymerase for dATP.

PGEM plasmid DNA was digested with Eco RV (NEB) overnight (10 µg pGEM DNA/6 µl Eco RV buffer/10 µg BSA/20 units Eco RV/81 µl H$_2$O). Digested DNA was precipitated in 0.5 M NaCl and 3 volumes of EtOH (−20° C.) for 3 hours at −20° C. and spun down. The pellet was resuspended in 100 µl H$_2$O and run on a gel to check the complete digestion. Then, the digested vector was incubated with Taq polymerase (Promega) (85 µl digested vector/10 µl Taq polymerase buffer/ 2 µl dTTP (100 mM)/3 µl Taq polymerase) to remove 3' overhang with its exonuclease activity. A drop of the mineral oil was overlaid and the mixture was incubated at 70° C. for 2 hours in a thermal cycler. Then, the sample was mixed with 2 volumes of phenol/chloroform/lsoamylalcohol and spun for 5 min at 14,000 rpm, followed by chloroform extraction. The supernatant was carefully mixed with 2 volumes of EtOH and incubated in −80° C. for 20 min. It was spun at full speed for 5 min and the resulting pellet was resuspended in 100 µl of 0.1× TE. The PCR products were then incubated with T-vector (2.5 µl 4×Ligation buffer/2 µl pGEM T-vector/1 µl PCR product/1 µl T$_4$ DNA ligase/4.5 µl H$_2$O) at 12° C. overnight. 4×Ligation buffer contained 400 mM Tris, pH 7.5, 80 mM DTT, 20 mM ATP, 40 mM MgCl$_2$, 400 µg/ml BSA and was stored at −20° C. Frozen DH5-α competent cells were thawed on ice. The ligation mixture containing 2 µl of β-Me, 3 µl of Ligase, and 50 µl of DH5 α cells was prepared and incubated on ice for 30 min, followed by heating at 42° C. for exactly 60 sec. The tube was immediately chilled on ice for 2 min. 450 µl of LB was added and incubated at 37° C. for 1 hour at 250 rpm in a shaker. A quarter of mixture was plated on X-gal/IPTG/Amp plate, and the plate was incubated at 37° C. overnight. And over 50 clones were initially analyzed by restriction endonuclease mapping followed by sequencing data from each end of the cDNA using vector sequences as primer sites.

DNA Sequencing

Supercoiled template DNA (3 µg) was resuspended in 18 µl of TE, pH 8.0. The sample was incubated for 5 min at room temperature after adding 2 µl of 2 M NaOH to denature the template DNA. Then, 8 µl of 5 M NH$_4$OAc, pH 7.5 and 100 µl of EtOH were added and incubated for 15 min on ice. The denatured DNA was pelleted and dried under vacuum. Dried DNA was resuspended in 7 µl of H$_2$O and mixed with 1 µl of primer (0.5 pmol/µl) and 2 µl of 5×Sequenase buffer. The mixture was incubated at 65° C. for 2 min and cooled to RT. Diluted labeling mix, DTT, α-[$^{32}$P]dATP, and diluted sequenase were added and incubated at room temperature for 2 min. Termination mixtures were added to 4 aliquots (A,C,G,T) and incubated at 42° C. for 2 min. To each tube stop solution was added and the samples were heated at 95° C. for 2 min before loading on gel. The samples were separated on 6% acrylamide gel at constant power 35 W for the time required getting optimal resolution of the sequence of interest. After running, the gel was placed on a piece of 3 MM paper and covered with Saran wrap. The gel was then dried for 30 min at 80° C. under vacuum drier (Bio-Rad) and exposed to Kodak X-Omat film overnight at RT. The sequence of the sample was read and analyzed using MacVector Sequencing Analysis Program.

EXAMPLE 4

Screening the cDNA Library

Preparation of Radioactive Probe

Plasmid DNA was isolated from a 500 ml culture of clone number 327 using the Maxi-prep kit (Promega). The inserts were isolated by digesting with restriction enzymes of Kpn I and Sac I from 50 µg of plasmid DNA. Plasmid DNA was digested with Sac I for 2 hours at 37° C. and precipitated with 95% EtOH overnight. Then the linerialized DNA was cut with Kpn I under the same condition. All of the DNA samples were run on a 1% Agarose gel and the inserts were isolated using low melting Agarose. After separating the inserts on gel, the gel was examined on the UV light illuminator and the location of the inserts was marked. Then the agarose gel toward the cathode side of the inserts were cut off using a blade and 1 % low melting agarose solution was poured into the window. The inserts were then electrophoresed into the low melting agarose region. The low melting agarose was excised and an equal volume of 2×Extraction buffer (400 mM NaCl/200 mM Tris, pH 7.9/2 mM EDTA) was added. The mixture was heated to 65° C.

for 15 min to melt the agarose block. The dissolved gel slices were combined in a tube and one volume of phenol/chloroform/Isoamylalcohol (25:24:1) was added, followed by chloroform/Isoamylalcohol. EtOH-precipitated insert DNA was dried under vacuum and resuspended in TE, pH 8.0. Isolated inserts were labeled using a Multiprime DNA Labeling Kit (Amersham). For one reaction, approximately 25 μg of DNA was used as a template. To the proper amount of DNA, water was added to 21 μl (in 50 μl reaction) and the mixture was heated in boiling water bath for 5 min, and then chilled on ice. While the template DNA was denaturing the reaction was set up (4 μl unlabeled dNTPs/5 μl Reaction buffer/5 μl primer/2 μl Klenow DNA polymerase/50 μCi [α-$^{32}$P]dCTP, 3,000 mCi/ml) and mixed together gently by pipetting up and down. The reaction was incubated at 37° C. for 30 min and 100 μl of STE (100 mM NaCl/10 mM Tris, pH 8.0/1 mM EDTA, pH 8.0) was added to stop the reaction. The labeled DNA was separated using spun-column chromatography. The column was made in 1 ml disposable syringe (Becton-Dickinson). The syringe was plugged with a small amount of sterile glass wool (Alltech Associates) and filled with STE equilibrated P-10 (Bio-Rad). The syringe was inserted in 15 ml centrifuge tube and spun at 1,500 rpm for 1 min. The gel was packed down this way until the volume of the packed beads was 0.9 ml. The column was washed with 100 μl of STE twice. A decapped Eppendorf tube was placed at the bottom of the centrifuge tube and the column was placed into the tube. The needle end of the syringe fitted into the mouth of the Eppendorf tube. The radioactive sample was loaded and spun at 1,500 rpm for 1 min to separate the free nucleotide from the labeled probe. The effluent was transferred to a new Eppendorf tube and the volume was measured. Incorporation rate of the labeled nucleotide was calculated by measuring the radioactivity of 1 μl of sample before and after passing through the column. The labeled DNA was used as a probe to screen cDNA library, Southern, and Northern blottings.

To clone the farnesyl pyrophosphate synthase gene, bacteriophages containing sunflower cDNA were prepared and used for screening. Duplicates of filters were prepared and well-isolates coincident plaques were picked and the inserts sequenced. This has led to the determination of the novel gene depicted below, which encodes farnesyl pyrophosphate synthase. We have cloned one FPS from sunflower and registered to GenBank, the accession number is AF019892 (Sunflower FPS). FASTAn searches show that nucleotide sequence is similar to other reported FPS family, 87% homology of tobacco FPS.

An examination of all clones FPS enzymes revealed a conserved amino acid. 50 clones were initially analyzed by restriction endonuclease mapping followed by sequencing data from each end of the cDNA using vector sequences as primer sites. From these clones we selected and characterized a cDNA, sun-FPS, encodes a FPS enzyme which converts DMAPP to FPP for synthesis of sterols, farnesylated proteins, and high chain length isoprenoid diphosphates. The sun-FPS1 (1347bp) cDNAs encode Mr 32,000 protein SEQ ID NO: 2) containing 346 amino acids, with a typical DDXXD motif (D:Asp, 93–97 amino acids, 232–236 amino acids) that is a characteristic of prenyltransfrases.

EXAMPLE 5
Assaying for Enzymatically Active Fusion Proteins Using Thermal Sensitive Yeast Mutants As nucleotide sequencing analysis was completed, an expression vector was constructed using pRSET fusion protein system for protein expression and pYES2 for yeast complementation assay. The SFPS protein was overexpressed and partially purified and size of the products was checked. Its enzymatic function was checked by *Saccharomyces cerevisiae* FPS mutant complementation assay. The DNA fragment encoding SFPS subcloned in PGEM vector was amplified by PCR using a pair of modified oligos, 75-s CGG GAT CCA TGG CCT CTG A TC TCA AGT C (residues 17–36 of SEQ ID NO:1) and BIEN TCG CGA GGC GAA TTG GGT ACC GGG GGG (SEQ ID NO:5). PCR products were subcloned back to pGEM vector. Ten positive clones were selected and grown in LB media. The inserts were checked by EcoRI digestion. Real positive clones were picked and frozen glycerol stocks were made. 50 III of frozen pRSET-SFPS stock was inoculated in 50 ml of LB containing 50 μl/ml ampicillin and incubated at 37° C. on the shaker overnight. The pre-culture was then inoculated in 500 ml of pre-warmed LB/Amp. When the $OD_{600}$ reached to 0.6–0.8, 2 ml of 100 mM IPTG was added to activate the Lac operon. The culture was incubated for 4 more hours and harvested at 2,000 rpm for 15 min. Then the supernatant was carefully removed. The pellets were resuspended in 15 ml of Lysis buffer containing 50 mM Tris, pH 8.0, 5 mM EDTA, 10% glycerol, and 0.2% NP-40. Cell suspension was sonicated 4 times, 30 seconds each time the power 5 on a scale 10 using Sonicator (Branson) and spun at 12,000 rpm for 30 minutes. The supernatant was recovered and filtered through a 0.45 μm filter (Amicon). Level of induction of sfps protein was checked by running a gel of the protein extracts.

10% PAGE was utilized in this study. The lower gel was made using a gradient maker (Hoeffer Sci.). A gradient maker was placed on the magnetic stirrer at setting 3 on a scale 10. 10% gel mixture (2.2 ml $H_2O$/2.9 ml 2 M Tris buffer, pH 8.8/2.6 ml 30% acrylamide/40 μl 10% ammonium persulfate/40 μl 20% SDS/10 μl TEMED for 7.8 ml gel solution) was added into the lower concentration chamber and mixed with 20% gel solution (0.2 ml $H_2O$/2.9 ml 2 M Tris, pH 8.8/4.6 ml 30% acrylamide/40 μl 10% ammonium persulfate/10 μl TEMED for 7.8 ml gel solution) in the gradient maker. The mixture was pumped by two peristaltic pumps (Pharmacia) into a mini gel cassette (Bio-Rad). The lower gel should be set in 30 minutes at room temperature. The gel solution was filled into two sandwiches to a level about 2 cm from the tops. The slabs were overlaid with the water-saturated n-Button with a greased syringe with 22 gauge needle. Gently apply about 0.3 ml of overlay. Repeat the other side of the slab next to the other spacer. The butanol layers were set evenly across the entire surface after a minute. A very sharp butanol-gel interface was visible when the gel was polymerized. The lower gel can be poured the night before use and stored at room temperature after covering with a strip of Parafilm on its top. The butanol layer was poured off by tilting the casting stand. The surface of the gel was rinsed with 20 ml of distilled water. Then 3 ml of gel overlay buffer containing 0.5 M Tris-HCI, pH 8.8 and 0.1% SDS in water was added and allowed to sit at least one hour. The gel overlay solution was removed using a syringe with 22 gauge needle. Upper stacking gel (1.1 ml of $H_2O$/0.4 ml 4×Upper Tris/0.15 ml 30% acrylamide/8 μl 10% ammonium persulfate/3.3 μl TEMED for a volume of 5 ml) was made and 0.5 ml of it was used for washing the top of the stacking gel before adding AP and TEMED. The gel solution was tilted few times and poured off from the gel cassette. Upper well-former comb was left in place until the samples were ready to be loaded. Each well immediately was washed after removing the upper well-former comb with reservoir buffer using 10 ml syringe with 22 gauge needle. Samples containing 10 to 15 μg protein and prestained low molecular weight markers (Bio-Rad) in sample buffer were adjusted to 1% β-mercaptoethanol and 3% SDS. Then they were heated at 65° C. for 15 min before loading. Desired amount of samples were then loaded with Pipetman attached PAGE loading tips. The gel was run at 10 mA constant current/gel cassette until the dye front had just moved into the resolving (lower) gel, then the current was turned up to 20–25 mA/gel. Run until the dye front was reached 0.5 cm from the bottom. The distinct overexpressed protein band was observed in the Coomasie blue staining gel at 31,000 Da corresponds with the predicted molecular mass of the FPS. The protein profile is shown in FIG. 1

Yeast Complementation Assay on of FPS

Figure 2:
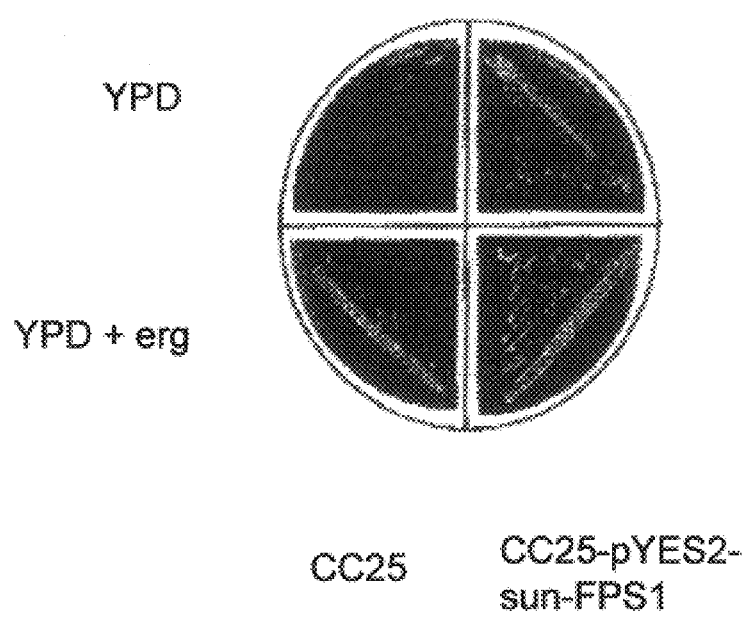
FIG. 2 depicts the rescue assay of the SFPS in yeast CC25 mutants.

To check if the sun-FPS1 encodes a functional enzyme, the cDNA was expressed in the mutant yeast (Saccharomyces cerevisiae) strain CC25, which is a temperature sensitive mutant strain that carries the leaky mutation erg20-2. Therefore this mutant is auxotrophic for ergosterol at a nonpermissive temperature (36° C.). An expression vector pYES2-SFPS in Bam HI and Xho I sites was constructed. Mutant yeast was transformed with pYES2-sun-FPS1, carrying a sunflower FPS1 cDNA under the control of the GAL1 promoter. As shown in FIG. 2, the ergosterol auxotrophy of the yeast mutants was complemented by the plasmid pYES2-sun-FPS1 at 36° C. The presence of FPS DNA in the rescued yeast were checked by PCR amplification and reveals that this introduced protein is able to replace yeast FPS enzyme activity and even restore following biochemical steps.

EXAMPLE 6

Plasmid Construction of SFPS and Transformation

As mentioned earlier, FPP is the precursor of the structurally diverse class of sesquiterpenoids and lies at a multiple branch point of the isoprenoid pathway, especially steroidogenesis and carotenogenesis. The isolation of the FPS cDNA and the description of the gene have made it possible to perform the effects of overexpression in different host systems. To measure to SFPS enzyme activity in vivo and to investigate the effects of the FPS overexpression to either steroidogenesis or carotenogenesis we constructed an agrobacterium-pCIP-SFPS binary vector to generate transgenic tobacco plants. The pCIP-SFPS binary vector was deposited with the Korean Collection for Type Culture (K.C.T.C.), designated KCTC 0520BP, KCTC, KRIBB #52, Oun-dong, Ysong-ku, Taejon 305-333, Republic of Korea under the terms of the Budapest Treaty. It is also necessary to determine whether SFPS 1 is functional in vivo and overexpression in sunflower itself works. positively in metabolism and, thus, the recombinant Agrobacterium clones (pCIP-SFPS) encoding FPS-enzyme now was constructed for generating transgenic plants.

A. Generation of the Transgenic Sunflower Farnesyl Pyrophosphate Synthase (SFPS) Tobacco.

As mentioned earlier, FPP is the precursor of the structurally diverse class of sesquiterpenoids and lies at a multiple branch point of the isoprenoid pathway, especially in steroidogenesis and carotenogenesis. To measure the SFPS enzyme activity in vivo and to investigate the effects of the FPS overexpression to a target plant, we constructed an agrobacterium-pCIP-SFPS binary vector and generated the transgenic tobacco plants. The 850 base pairs of insert in pGEM vector was cut out with Bam HI and Nru I and purified from a agarose gel after 1% TAE-agarose gel running using gel purification kit (Qiagen). PBI121 digested with Bam HI and Nru I and the purified insert DNA fragment was mixed with DNA ligase with an appropriate buffer and incubated at 16° C. overnight. One positive clone (clone #668) checked by restriction enzyme digestion after midi scale preparation was used for Agrobacterium transformation. Wild tobacco plants grown on MS-agar media was collected and sanitized. Agrobacterium strain LBA4404 was grown in LB (5 g salt/L) until late log/early stationary phase. Pellet cells and resuspend to $OD_{600}$=0.8 in 10 mM $MgCl_2$, 5% sucrose, 0.005% Silwet L-77. Sanitized leaves were submerged in Agrobacterium suspension and cut by scalpel. After submerging in Agrobacterium suspension for 15 minutes, leaf discs were transferred in the shooting MS media (sucrose, vitamin, NAA, 0.1 mg/L and BA, 1 mg/L). After incubating for three days in dark condition at 25° C. incubator, remaining Agrobacterium was rinsed off with autoclaved distilled water and leaf discs were transferred to a fresh MS agar plate (sucrose, vitamin, carbenecillin, 250 mg/L, kanamycin 100 mg/L, NAA, 0.1 mg/L and BA, 1 mg/L). Subcultures were made every week during next four weeks with increased amount of kanamycin for transformants selection. When shoots came out, they were transferred to fresh MS stabilizing media (sucrose, vitamin, carbenecillin, 250 mg/L, and kanamycin 200 mg/L) and left for 2 weeks. Selected transformants were transferred to root induction media (½ MS and sucrose) until roots come out. After three to four weeks, survived transgenic tobacco plants were transplanted in soil and grown at 27° C. green house.

B. Characterization of the Transgenic Tobacco

To verify the expression of the introduced SFPS in different transgenic tobacco plants, genomic DNA samples were purified. To isolate genomic DNA from transgenic tobacco plants, freeze-thaw method was used. Flash frozen leaves were ground in liquid nitrogen cooled mortar-pestle and transferred in clean 25 ml Corex tubes. Lysis buffer (20 mM Tris, pH 8.0/100 mM EDTA/100 μg/ml Proteinase K), and SDS was added to 0.5%. The mixture was incubated at 70° C. for 15 min, followed by addition of Proteinase K to a final concentration of 200 μg/ml and incubated at 37° C. overnight. After incubation, equal volume of Tris buffer-saturated phenol was added, followed by an equal volume of chroloform: isoamylalcohol (24:1) and mixed on Lab Quake for 1 hour. The sample was vortexed at full speed and spun at 14,000 rpm for 5 min. The upper phase was transferred to a new tube and added 400 μl of chloroform isoamylalcohol. After brief vortexing, the sample was spun and the upper phase was saved in a new tube. One tenth volume of 3 M Sodium acetate, pH 8.0 and two volumes of absolute EtOH (−20° C.) were added and mixed gently back and forth. Then the tube was incubated over night at −20° C. DNA was pelleted by spinning at 5,000 rpm for 5 min at 4° C. After spinning, supernatant was discarded carefully with a vacuum connected drawn-out Pasteur pipette. One milliliter of 70% EtOH (−20° C.) was added, washed, spun, and removed. The pellet was then dried on a speed vac (Savant) under vacuum to evaporate off the excess EtOH. The DNA was then suspended in 50~100 μl of TE, pH 8.0 (10 mM Tris, pH 8.0/1 mM EDTA) checked and quantitated. Same oligonucleotides used for the subcloning SFPS insert were used for PCR amplification at a high stringency condition. PCR products generated from samples of transgenic tobacco plants were then digested with Xba I, which will generate 760 base pairs and 150 base pair fragments. Selected transgenic tobacco plants with those fragments were grown further and expression level of introduced SFPS in the transgenic tobacco plants was checked by Northern blotting.

Northern Blot

Total RNA samples were purified using Tri reagent (Sigma). Finally, the pellet was resuspended in 400 μl of distilled H$_2$O treated with DEPC (diethylpyrocarbonate), and quantitated by reading the absorption of a 100-fold dilution at 260 nm on a Beckman Du 8 spectrophotometer.

Figure 3:
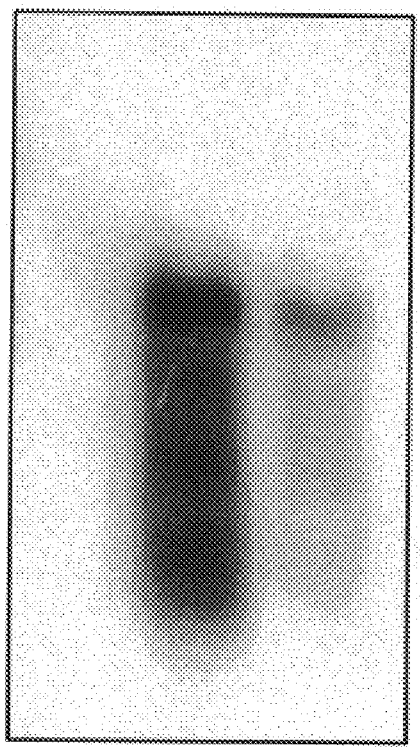
FIG. 3 depicts the expression of the SFPS in the transgenic tobacco plants. Total RNA samples from different transgenic tobacco plants were purified and probed with $^{32}$P-random primed SFPS.

Native analytical gels containing 1.5 µg of RNA from each sample of isolated RNA were run to assure that degradation had not occurred. After this, aliquots containing 10 µg of random total RNA were separated electrophoretically and transferred onto Nytran membrane. The RNA was transferred onto Nytran that had been wetted in distilled H$_2$O and soaked in 20×SSPE for 15 min. The transfer was carried out in an apparatus similar to that used for Southern transfers for 24 hours, with 20×SSPE as the transfer buffer. Deglyoxylation of the transferred RNAs was accomplished by incubating the membranes in 0.02 M Tris, pH 8.0 at 100° C., for 5 min. Radioactive SFPS probe generated as above were used for this experiment. Prehybridizations, hybridizations, and washes for RNA:DNA hybridizations were done as described for DNA:DNA hybridizations. Autoradiography was also carried out as with Southern hybridizations. Northern blot analysis shows that the mRNA encoding sun-FPS1 is of high abundance, and the messages were present in the leaf and stem (FIG. 3).

Overexpression of FPS results the delayed senescence in aged plants and few parameters of the delayed senescence were examined, including chlorophyll content, relative amount of the of Rubisco, and cyeteine protease. Leaf senescence is known to be an active, regulatory developmental process ultimately resulting in cell death during which valuable metabolites are recovered for use by the growing (Weaver et al, 1998). Decline of photosynthetic activity is observed as the cells are stripped of their components and the contents of protein and nucleic acid drops several folds and starch and lipids are metabolized (Lers et al., 1998).

EXAMPLE 7

Figure 4A:
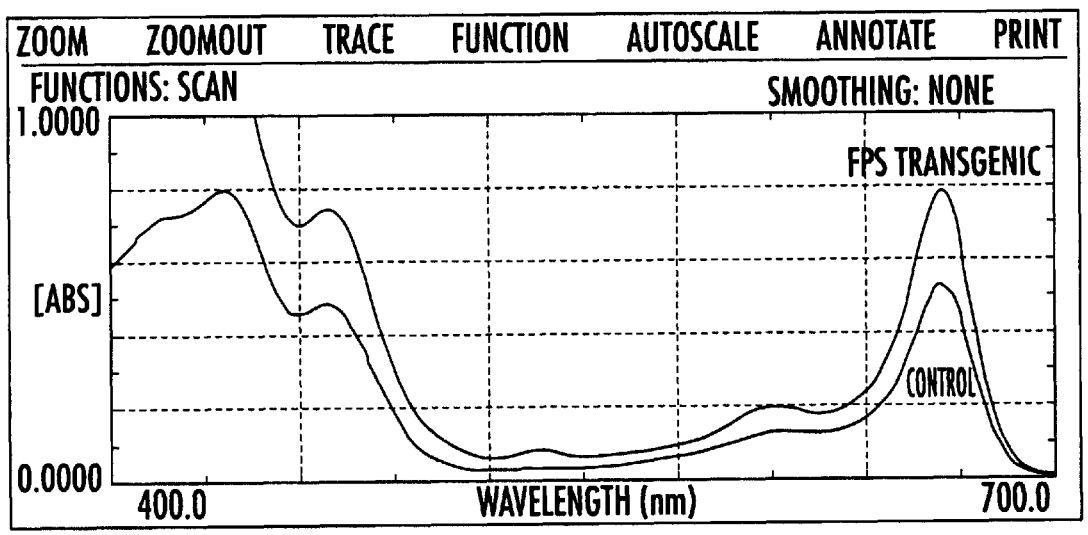
FIGS. 4A–4B depict spectrophotometric determination of chlorophylls in plant extracts performed on two sets of samples; whole plants of (a) four-week-old transgenic and non-transgenic tobaccos, and (b) three-month-old leaves of seven-month-old transgenic and four-month-old non-transgenic tobacco plants.
Figure 4B:
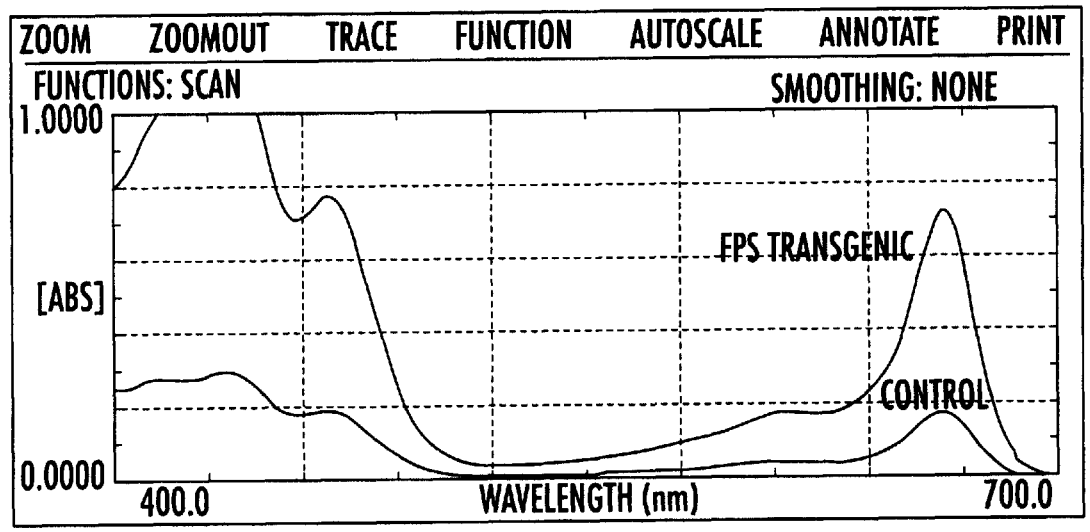
Figure 5A:
FIGS. 5A–5C depict (a) Comparison of FPS-transgenic and control tobacco plants. Note Leaf greenness after seed setting. (b) Seed collections of FPS-transgenic and control tobacco plants. (c) Seven-month-old FPS-transgenic and four-month-old control tobacco plants. Picture was taken seven months after transplanting to soil.
Figure 5B:
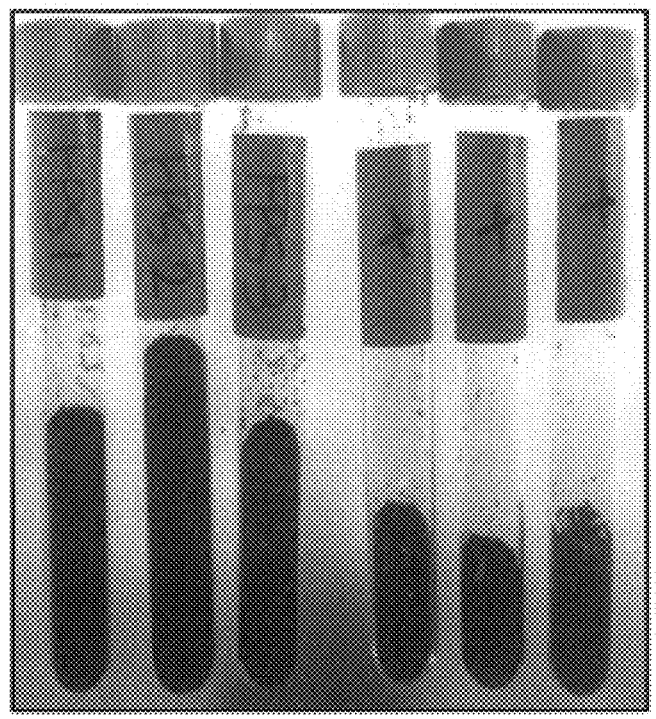
Figure 5C:
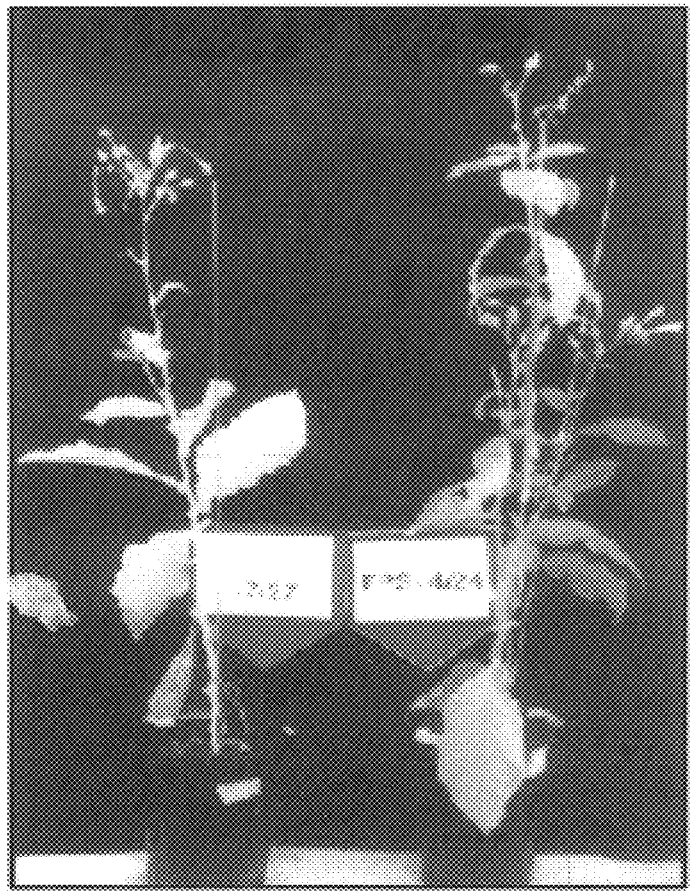

Measurements of Chlorophyll Contents in the Leaves of the SFPS Overexpressing Transgenic Tobacco Plants Growth of transgenic and non-transgenic plants was monitored and there was no significant difference in their growth of transgenic and non-transgenic plants except darker pigmentation of transgenic one (FIG. 4a, and 4b). Spectrophotometric determination of the chlorophylls in plant extracts were done on two sets of samples; whole plants of the four-week-old transgenic and non-transgenic tobaccos, and three-month-old leaves of seven-month-old transgenic and four-month-old non-transgenic tobacco plants. Transgenic ones in both cases showed darker pigmentation comparing to control ones. Boltings in both groups started within few days. One drastic feature observed in the transgenic one is "prolonged delayed senescence" (FIG. 5a and 5b). As shown in FIG. 5 transgenic one continuously showed the "greenness" until seed collection time. The greenness lasted longer than normal plant, and extra numbers of axillary buds and new shoots emerged from the bottom of the branch, due to apical dominance, resulted the extra numbers of flowers and its products, seeds (FIG. 5c). This long lasting juvenility may be the consequence of higher level of gibberellin by fpp overproduction. While some of these morphological changes result directly from the localized overproduction of gibberellin, other changes probably result from the mobilization of plant nutrients to tissues rich in gibberellin.

EXAMPLE 8

Figure 6:
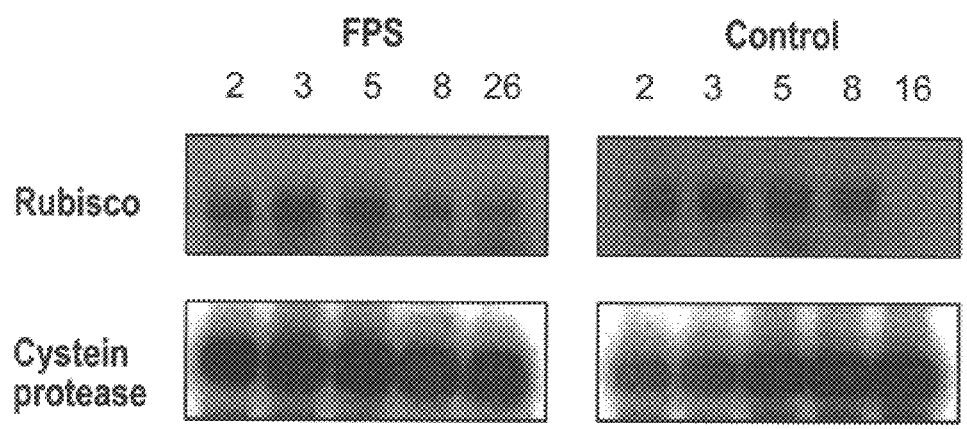
FIG. 6 depicts the expression patterns of mRNAs for senescence-related cysteine protease and ribulose-1, 5bisphosphate carboxylase/oxygenase.

Characterization of the Features of the SFPS Overexpressing Transgenic Tobacco Plants Expression Patterns of Senescence-associated Genes In general, control of senescence is done by nucleus. Though senescence is the series of degrading processes of many components, protein synthesis is required. mRNAs encoding photosynthetic proteins, CAB and Rubisco are known to decline in abundance during senescence (He et al., 1997) and some mRNAs, cysteine protease, malate synthase, and glutamine synthase, showed increase in abundance (Ding et al., 1993; Oh et al., 1997). The expression of a couple of senescence-associated gene (SAGs), Rubisco and cysteine protease in transgenic and non-transgenic tobaccos was compared in response to age. Individual SAGs differed from the norms in different ways, however, suggesting that their gene products play a role in overlapping but not identical circumstances (He et al., 1997). For Northern blot analysis, 2, 3, 5, 8, and 23 weeks old transgenic plants and 2, 3, 5, 8, and 16 weeks old non-transgenic tobaccos were processed to isolate total RNA samples. End-labeled cysteine protease oligos were used as a probe. Northern analysis showed that the mRNA levels of cysteine protease gradually increased during leaf senescence in non-transgenic ones (FIG. 6a). However, SFPS-transgenic plants showed rather constant level of the cysteine protease in all samples. As seen in FIG. 6b, expression level of Rubisco remains high throughout the 23 weeks old transgenic plant, but the signal gets weaker in non-transgenic plant. In summary, transgenic tobacco plants with an SFPS shows, compared with the wild type, higher contents of chlorophyll, higher and long lasting Rubisco contents, and constant level of cysteine protease, while the control plants confirm the reported results. Due to unidentified reasons, transgenic tobacco plants maintain their juvenility in their stems and leaves, presumably by overproduced gibberellins, and apical dominance retains and results continuous axillary budding, higher number of flowers, and higher seed yields.

What is claimed:

1. A method for increasing chlorophyll content, vegetative growth, and seed yield and delaying leaf senescence in tobacco plants comprising the steps of:
   a) introducing into tobacco cells, a recombinant plant expression vector comprising an isolated nucleic acid according to SEQ ID NO: 1 operably linked to a promoter, thereby producing transformed plant cells; and
   b) regenerating from the transformed cells, whole transgenic plants that have an increase in chlorophyll content, vegetative growth, and seed yield, and a delay in leaf senescence.

2. The method of claim 1 wherein said recombinant plant expression vector is pCIP-sfps (KCTC Accession No. 0520BP).

3. The method of claim 1, wherein said promoter is selected from the group consisting of a bacterial promoter, a viral promoter and a plant promoter.

4. A transgenic tobacco plant produced by the method of claim 1.

5. A transgenic tobacco plant comprising a nucleic acid which encodes SEQ ID NO:2.

6. An expression vector comprising a promoter operably linked to the nucleic acid of SEQ ID NO: 1.

7. The expression vector of claim 6 wherein said promoter is selected from the group consisting of a bacteria promoter, a viral promoter and a plant promoter.

8. The expression vector according to claim 6 wherein said vector is capable of being transferred into and replicated in a bacterial, fungal, or plant host.

9. A microorganism containing the expression vector according to claim 6 wherein said microorganism is *Agrobacterium tumefaciens*.

10. A transformed host comprising the expression vector of claim 6 wherein said transformed host is selected from group consisting of a plant, a bacterium, and a yeast.

11. A process for the production of farnesyl pyrophosphate synthase in vitro comprising the steps of:
    a) producing an expression vector which comprises a promoter operably linked to a nucleic acid having the sequence of SEQ ID NO: 1;
    b) transferring said expression vector into a host cell thereby producing a transformed host cell; and
    c) growing said transformed host cell in vitro and isolating said farnesyl pyrophosphate synthase.

12. A process for the production of farnesyl pyrophosphate synthase comprising the steps of:
    a) producing an expression vector which comprises a promoter operably linked to a nucleic acid having the sequence of SEQ ID NO: 1;
    b) introducing said expression vector into a cell thereby producing a transformed cell wherein said transformed cell is selected from the group consisting of a plant cell, a bacterial cell; and a yeast cell; and
    c) growing said transformed cell and isolating said farnesyl pyrophosphate synthase.

13. The process according to claim 12 wherein said transformed cell is a plant cell.

14. The process according to claim 12 wherein said plant cell is selected from the group consisting of a tobacco plant cell, a grass plant cell, and a perennial plant cell.

* * * * *